United States Patent [19]

McQuilkin

[11] Patent Number: 4,542,532
[45] Date of Patent: Sep. 17, 1985

[54] DUAL-ANTENNA TRANSCEIVER

[75] Inventor: Gary L. McQuilkin, New Hope, Minn.

[73] Assignee: Medtronic, Inc., Minneapolis, Mich.

[21] Appl. No.: 587,754

[22] Filed: Mar. 9, 1984

[51] Int. Cl.⁴ .............................................. H04B 1/44
[52] U.S. Cl. ......................................... 455/78; 455/41; 455/82
[58] Field of Search ....................... 455/41, 78, 79, 82, 455/83; 179/82; 128/903; 370/32; 333/100, 118, 132, 175

[56] References Cited

U.S. PATENT DOCUMENTS

| 3,102,991 | 9/1963 | Jess ........................................ 455/82 |
| 3,117,241 | 1/1964 | Paynter et al. ........................ 455/82 |
| 3,227,954 | 1/1966 | Fichter, Jr. ............................ 455/82 |

Primary Examiner—Jin F. Ng
Attorney, Agent, or Firm—Glenn W. Bowen; John L. Rooney; Joseph F. Breimayer

[57] ABSTRACT

A magnetic-field, noise-cancelling transceiver is provided by a dual-coil antenna circuit. In the receive mode, two identical coils, connected in series opposition, cancel noise signals common to both coils and receive desired signals present at only one coil. Capacitance in parallel with the series-opposed coils establishes the resonant frequency of the receiver, antenna circuit. In the transmit mode, the two coils, connected in series opposition, have their non-adjacent terminals clamped to ground via two pairs of oppositely-poled diodes, one pair on each non-adjacent terminal. The transmitter signal, coupled to the junction of the two coils through a capacitor, generates additive magnetic fields by causing equal currents to flow in each coil from the common junction, to their respective diode junctions, to ground through the respective, oppositely-poled diode pairs. Series resonance is established by the transmitter coupling capacitance and the parallel combination of the two coils. The transmitter and receiver tuning are independent. The receiver tuning is unaffected by the transmitter circuitry and coupling capacitance because the transmitter is connected to the null between the receiving antenna coils. The transmitter tuning is unaffected by the receiver circuitry and receiver capacitance because the diode pairs provide a relative short across the receiver input during transmission.

10 Claims, 1 Drawing Figure

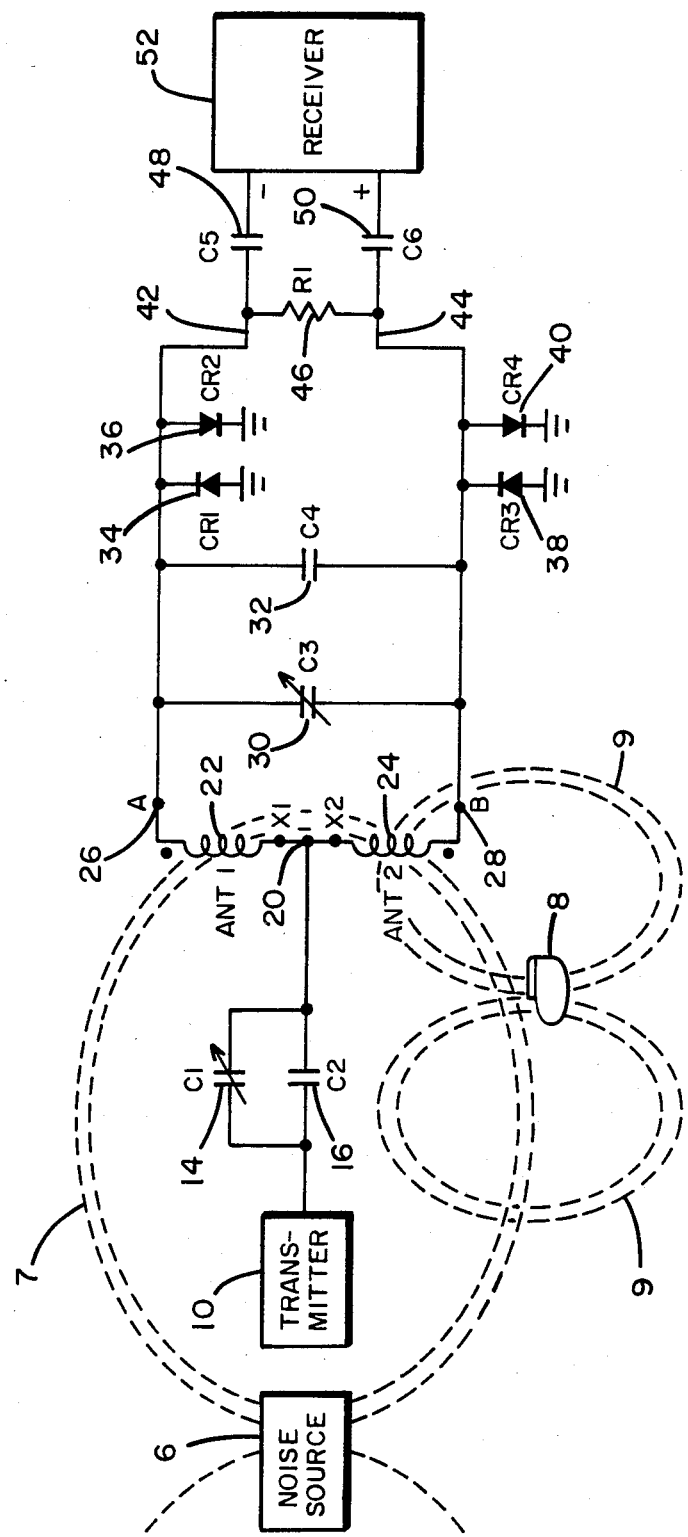

DUAL-ANTENNA TRANSCEIVER

BACKGROUND OF THE INVENTION

The invention relates generally to two-way communication devices which must operate in an environment with electromagnetic interference. More specifically, the invention relates to external transceivers which remotely communicate with implanted medical devices. Part of this two-way communication link consists of control or programming signals transmitted from the external device to the implanted device for the purpose of altering the operation of the implanted device. The remainder of the link consists of low-level telemetry transmissions from the implant to the external device for the purpose of conveying information such as current status, battery level, or patient data.

Two-way communication with implanted medical devices imposes special problems which become even more acute in an interference-prone environment, especially where the medical devices are essential to maintaining life functions. Necessarily, implanted medical devices require ultra-low power levels from long-lived batteries. The most common implanted telemetry system employs a single, multi-turned coil to externally receive the low-level telemetry signals. These single-coil, receiving antennas are quite susceptible to interference from electric, magnetic and electromagnetic field sources which are present in the clinical environment.

Many implanted telemetry systems employ two separate external coils, one for transmission of control or programming information to the implanted device and the other to receive telemetry data from the implanted device. As a consequence, the tuning of the receiving and the transmitting circuits of the external transceiver are interdependent due to the close proximity of the two coils.

The present invention employs two noise-cancelling, antenna coils, which improve the signal-to-noise ratio significantly, and a circuit which permits transmission and reception of signals through the same antenna coil network without interactive tuning problems and without the employment of any switching devices. The improved, external transceiver circuit permits two-way communications with implanted medical devices in close proximity (on the order of 4 inches to 2 feet) to common interference sources such as cathode ray tubes and video monitors.

DESCRIPTION OF THE DRAWING

The present invention is illustrated by reference to the drawing which is a schematic of a dual-antenna transceiver that is positioned near an implanted medical device and farther from an external noise source, in order to illustrate the operation of the transceiver.

TECHNICAL DESCRIPTION OF THE INVENTION

The dual antenna transceiver design of the present invention provides a two-way communication system which may be operated with ultra-low powered implanted medical devices. With this antenna and the transceiver control design, both analog and digital data may be telemetered out from the implanted device, for example, by use of pulse-interval modulation. In a similar manner programming data and commands can be transmitted from the external equipment to the implanted device. In general, this type of system encounters a number of substantial problems which must be overcome to provide an effective system. These include:

A. Weak telemetry signals from the implanted device.

Transmitters within implanted medical devices usually have ultra-low power constraints since the implant must be powered for many years from a single battery source. In addition, biocompatability is achieved in modern implants by use of laser-welded, titanium cases which further attenuate telemetry signals radiated from the implanted device. As a result of the power restrictions and case attenuation, a very sensitive telemetry receiver is required to externally detect the extremely weak telemetry signals.

B. Numerous interference sources exist in a hospital environment.

Modern hospitals contain electronic equipment which can radiate magnetic fields in the telemetry passband which is commonly used. For example, one implanted telemetry system employs a center frequency of 175 KHz with a band width of 25 KHz. Equipment such as cathode rate tubes, video monitors, thermal printers and many other types of equipment now used in hospitals can generate in-band interference as close as 2 feet from the telemetry receiver.

C. Random phase interference may cancel the telemetry signal at the receiving antenna.

Because the telemetry signal and interference signals are not phase-locked, the amplitude and polarity of the interference signal can periodically establish a condition which cancels the telemetry-signal field at the receiving antenna. This condition cannot be resolved by sophisticated electronic filtering and signal processing because the signal is not initially picked up by the antenna.

D. Relatively strong programming signals are required by implanted programmable devices.

In order to avoid electro-magnetic interference problems in programming the implanted device, reliable programming is achieved by employing a substantially strong programming signal or by specially designed security circuits. For example, a security system for programming is presently employed in which a magnetic reed switch must first be closed to supply power to the input receiver, and to permit reception of a digitally encoded access and programming code. In order to assure reliable re-programming when desired, the external transmitter must be capable of generating strong magnetic fields 3–4 inches from the transmitting antenna. However, radiated fields must also conform to acceptable regulatory emission levels.

E. Receiver and transmitter tuning should be independent.

Total independence of receiver tuning and transmitter tuning is highly desirable from a manufacturing standpoint and from an operational standpoint. Dependency between receiver and transmitter tuning creates difficulties during initial calibration and also during field service.

The dual-antenna transceiver circuit described herein provides a number of advantages over prior antenna circuits. These include:

(1) A 24–30 db improved noise rejection over a single-coil antenna for in-band, spatially-aligned, interference fields generated by sources several feet from the antenna.

(2) There is independent tuning of transmitter and receiver antenna circuits.

(3) No switches are required to achieve independent tuning of transmitter and receiver, thereby reducing the component count and increasing reliability of the device because no active switching device is employed.

(4) Switching transients generated by active switching devices are avoided.

(5) An additional 30 db rejection of interference can be obtained when the interference field is aligned normal to the antenna coil axis.

(6) Reception of valid telemetry signals are permitted within 4 inches to 2 feet of typical cathode ray tubes or video monitors, while single coil antennas in contrast may detect interference as far as 3–6 feet from said devices with the same signal levels.

The dual-antenna transceiver of the present invention is described by a reference to the drawing in which the transmitter 10 of the transceiver has its output connected to a parallel combination of a fixed resonant capacitor 16 and an adjustable resonant capacitor 14, which is used for resonating the antenna at the transmitter frequency. The series-resonant capacitors are connected between the transmitter circuitry and the junction point 20. Junction point 20 lies between the two series-connected antenna coils 22 and 24. The two small black dots adjacent the junction points 26 and 28 indicate the polarity of winding of the coils 22 and 24. The winding polarity is such that the coils are in series-opposition.

Capacitors 30 and 32 are used to form a parallel resonant circuit with series-opposed coils 22 and 24. Capacitor 30 provides fine-tuning of this resonant frequency.

Four diodes are employed in the transceiving circuit, two of which are electrically coupled to the electrical junction point 26 and the other two of which are coupled to the junction point 28. Diode 34 has its cathode coupled to the junction point 26 and its anode coupled to ground while diode 36 has its anode coupled to the junction point 26 and its cathode coupled to ground. Similarly, diode 38 has its cathode connected to the junction point 28 and its anode connected to ground, while diode 40 has its anode connected to junction point 28 and its cathode connected to ground. Thus, any signals which are developed across the diode pair 34, 36 or the diode pair 38, 40 will be limited in magnitude to the voltage drops that may be developed across these diodes.

The cathode of the diode 34 and the anode of the diode 36 are connected by the line 42 to one end of an antenna load resistor 46. The diodes 34 and 36 may thus be said to be "oppositely-poled." The other end of the antenna load resistor 46 is connected by the line 44 to the cathode of the diode 38 and the anode of the diode 40.

The voltage developed across the load resistor 46 is coupled to the receiver 52 by the coupling capacitors 48 and 50. As previously mentioned, the field 9 from the implanted medical device 8 will have a stronger effect on coil 24 than on coil 22. When the device is in the receive mode the signal seen at the receiver input is the difference between the voltages generated across each individual coil. The receiver 52 desirably employs a differential amplifier input stage to avoid any noise introduction due to voltage differences between the antenna and system ground.

In the receiving mode, the antenna coil 24 which is closest to the implanted device picks up a substantially larger signal than the more remotely located coil 22.

For example, the implanted cardiac pacemaker 8 creates a field 9 when it is transmitting telemetry information which links the coil 24 with a substantially stronger signal than the coil 22. On the other hand, a noise source 6, positioned at a more remote location provides a field 7 which tends to link both coils, 22 and 24, with the same field. Since the coils are wound in series opposition, however, the noise field component from the noise source 6 will be cancelled, leaving primarily the signal component at the input of the receiver 52.

During telemetry reception all of the diodes are essentially non-conductive due to the low antenna signal voltages that are typically applied across the diodes. These are generally less than 5 millivolts peak-to-peak and, therefore, diodes 34, 36 and 38, 40 effectively act as very high resistances to ground. The interference field which links the antenna coils 22, 24 will generate equal but opposite antenna voltages which will cancel when summed at the receiver input and the common mode rejection of the receiver differential signal will also attenuate undesirable electric-field pick-up. The telemetry field thus generates antenna voltages unequally on the coils 22 and 24. Thus the telemetry signals appear at the input of the receiver 52 through the coupling capacitors 48 and 50. During the receive mode of operation, the transmitter circuit 10 will be effectively connected to a null point between the oppositely wound coils 22, 24 and will, thus, have no appreciable effect on the receiver circuit.

When the transceiver is in the transmit mode, however, typical antenna voltages of 250 volts peak-to-peak will create an effective short to ground at the junction points 26, 28 regardless of the polarity of the transmitted signal because of the diodes 34, 36 and 38, 40. Current will then flow through the parallel-connected capacitors 14, 16 and will divide through the coils 22, 24 to generate additive magnetic fields, since these elements form a thus series-resonant circuit. A large transmitted antenna signal may be developed even with battery-powered drive circuitry. The conducting diodes 34, 36 and 38, 40 have effectively removed the receiver 52 and the receiver tuning capacitors 32, 30 from the circuit when it is in the transmit mode. For maximum antenna voltages during transmissions, capacitors 30 and 32 should have dissipation factors less than 0.1%.

What is claimed is:

1. A dual-antenna transceiver comprising receiving means, transmitting means, first and second inductive means wound in series-opposition and coupled to a junction point, first capacitive means coupled between said transmitting means and said junction point wherein said first and second inductive means and said first capacitive means form a series resonant frequency at the transmission frequency of said transmitting means, said first inductive means being coupled to a first output point and said second inductive means being coupled to a second output point, and second capacitive means coupled across said first and second output points to form a parallel-resonant circuit with said first and second inductive means at the receiving frequency of said receiving means, said receiving means being coupled to said parallel-resonant circuit.

2. A dual-antenna transceiver as claimed in claim 1 further comprising signal limiting means coupled to said first and second output points for limiting signals from exceeding a predetermined maximum regardless of polarity.

3. A dual-antenna transceiver as claimed in claim 2 wherein said signal limiting means are voltage limiting means.

4. A dual-antenna transceiver as claimed in claim 3 wherein said signal limiting means are rectifier means.

5. A dual-antenna transceiver as claimed in claim 4 wherein said signal limiting means comprise oppositely-poled diodes.

6. A dual-antenna transceiver as claimed in claim 1 wherein said receiving means comprises differential input means coupled to receive and to differentially amplify the signals at said first and second output points.

7. A dual-antenna transceiver as claimed in claim 6 further comprising signal limiting means coupled to said first and second output points for limiting signals from exceeding a predetermined maximum regardless of polarity.

8. A dual-antenna transceiver as claimed in claim 7 wherein said signal limiting means are voltage limiting means.

9. A dual-antenna transceiver as claimed in claim 8 wherein said signal limiting means are rectifier means.

10. A dual-antenna transceiver as claimed in claim 9 wherein said signal limiting means comprise oppositely-poled diodes.

* * * * *